(12) United States Patent
Hurley

(10) Patent No.: US 8,088,088 B2
(45) Date of Patent: Jan. 3, 2012

(54) BACK SUPPORT SYSTEM

(76) Inventor: Patrick Timothy Hurley, San Diego, CA (US)

(*) Notice: Subject to any disclaimer, the term of this patent is extended or adjusted under 35 U.S.C. 154(b) by 642 days.

(21) Appl. No.: 12/273,920

(22) Filed: Nov. 19, 2008

(65) Prior Publication Data

US 2010/0125230 A1    May 20, 2010

(51) Int. Cl.
A61F 5/00      (2006.01)
A62B 35/00    (2006.01)

(52) U.S. Cl. .................................. 602/18; 119/857
(58) Field of Classification Search .............. 602/19, 602/5, 60–62; 119/847, 857, 700, 769, 770; 2/44; 482/124, 69, 70
See application file for complete search history.

(56) References Cited

U.S. PATENT DOCUMENTS

| | | | |
|---|---|---|---|
| 0,452,206 A | 5/1891 | Aaron | |
| 0,807,908 A | 12/1905 | Bradstreet | |
| 1,202,851 A * | 10/1916 | Kelly | 2/44 |
| 1,409,326 A * | 3/1922 | Williamson | 2/44 |
| 1,544,162 A | 6/1925 | La Vigne | |
| 1,634,621 A | 7/1927 | Martinez | |
| 3,295,517 A | 1/1967 | Stevens | |
| 3,570,011 A | 3/1971 | Naig | |
| 5,176,622 A | 1/1993 | Anderson et al. | |
| 5,643,184 A | 7/1997 | Toso | |
| 5,816,251 A | 10/1998 | Glisan | |
| 5,860,944 A * | 1/1999 | Hoffman, Jr. | 602/19 |
| 5,951,591 A | 9/1999 | Roberts | |
| 6,129,691 A * | 10/2000 | Ruppert | 602/19 |
| 6,436,065 B1 | 8/2002 | Mitchell | |
| 6,450,131 B1 * | 9/2002 | Broman | 119/857 |
| 1,371,690 A1 | 11/2008 | Kelly | |
| 7,553,266 B2 * | 6/2009 | Abdoli-Eramaki | 482/124 |

* cited by examiner

*Primary Examiner* — Kim M Lewis
(74) *Attorney, Agent, or Firm* — George S. Levy (57) ABSTRACT

A support system designed to reduce the stress exerted on the back of a wearer when he bends over to lift a load. It comprises a harness and a yoke for distributing the load on the shoulder of the wearer and a tension system equipped with elastic cables. It further comprises leggings including straps designed to wrap around the sole of the wearer and to maintain the force acting on the leg as close as possible to the bone structure of the leg of the wearer, thereby relieving stress on his back and along his legs.

17 Claims, 13 Drawing Sheets

BACK SUPPORT SYSTEM

FIELD OF THE INVENTION

The present invention relates to equipment for supporting, strengthening the back and reducing back strain in circumstances requiring bending at the waist. It also relates to equipment designed to prevent back injuries during bending or lifting activities.

BACKGROUND

Back injuries that result from bending at the waist and lifting heavy loads, besides being painful, difficult and costly to treat, cause the loss of millions of dollars in productivity. These injuries are caused by high twisting forces exerted on the spinal column by the cantilevered action of bending. The vertebras which occupy a few square inches of surface operate as a fulcrum in a lever system. The short segment of the lever system is located on the vertebras themselves. The long segment of the lever system includes the arms, the hands and the load itself. Therefore the force applied to this lever may be located feet away from the backbone. As a result tremendous forces are exerted on the vertebras and may cause injuries.

Prior art includes U.S. Pat. No. 6,450,131 by Daniel James Broman; U.S. Pat. No. 6,436,065 by Timothy John Mitchell; U.S. Pat. No. 6,129,691 by John F. Ruppert; U.S. Pat. No. 5,957,091 by Kurt D. McDonald and Timothy W. Ecker; U.S. Pat. No. 5,860,944 by Henry R. Hoffman Jr.; U.S. Pat. No. 1,634,621 by Isidoro Martinez; and U.S. Pat. No. 1,409,326 by Ernest S Williamson. The prior art does not address in a methodical, well thought out engineering approach, the problem of how to design a back support system that distributes tensile and compressive forces such as to minimize stress on the spinal column and on soft tissues. This invention solves this problem.

It is therefore an object of this invention to provide a back support system designed such that forces are mainly applied to the skeleton of the wearers rather than to his soft tissues.

It is another object of this invention to distribute forces such that compressive forces are mainly applied to the wearer's skeleton and tensile forces are mainly conveyed to the invention embodiment.

Further features, aspects, and advantages of the present invention over the prior art will be more fully understood when considered with respect to the following detailed description claims and accompanying drawings.

SUMMARY OF THE INVENTION

This invention is a back support system designed to reduce the stress exerted on the back of a wearer when he bends over to lift a load. This back support system comprises a harness which is secured to the torso of the wearer, by means of breast straps joined at the front of the wearer's chest. The harness also comprises two shoulder straps wrapped from front to back, over the shoulders of the wearer.

The back support also comprises a yoke system which includes two curved rails made of rigid material. The curved rails are attached to the shoulder strap, and are wrapped in their longitudinal directions over the shoulders of the wearer from front to back. In addition, both curved rails have their top surface configured in a concave shape in their perpendicular directions.

The back support also comprises a tension system which includes tension straps extending from front to back inside the concave surface of the curved rails. Both tension straps are attached at their top ends to the breast straps at points located at the front of the wearer's chest. The tension system also includes two elastic cables, each cable attached at its top end to one of the straps.

The back support system also includes a legging system comprised of a right legging net and a left legging net. The legging nets are worn on the legs of the wearer. Each legging net comprises a vertical strap attached at its two ends to the bottom of one of the elastic cable, in such a fashion as to form a vertical loop that wraps around the respective right or left sole of the wearer. In addition, the legging nets include at least one horizontal strap that fastens the vertical strap against the leg of the wearer essentially following the bone structure of his leg. Another foot strap fastens the vertical strap against the foot of the wearer.

The back support system generates a tension force when said wearer bends over to lift a load. This tension force counterbalances the force generated on the back of the wearer by the load, thereby relieving stress on his back. In addition, the tension system, maintains the tensile force essentially aligned along the bone structure of the leg of the wearer thereby relieving stress along his legs.

This invention includes several variations such as fastening and adjusting buckles to fit wearer's of different sizes. The curved rails can be made with an upper surface concave in the perpendicular direction of the rail. The concavity could be obtuse or extreme such as to form a tube slotted along the length of the rail. The elastic cable could be made of surgical tubing configured such that the ends of the tubing are joined together to form a loop. The surgical tubing may be reinforced at their point of contact with the tension straps and with the legging nets by rigid u-shaped tubing. Carabiners could be used to join the elastic cable to the legging nets. Fastening and adjusting buckles may be replaced by VELCRO™ fasteners. D-shaped rings can be used to keep the tension straps firmly inside the rails. A horizontal strap can be used to join together the tension straps to prevent them for sliding off the rails.

DETAILED DESCRIPTION

Figure 1:
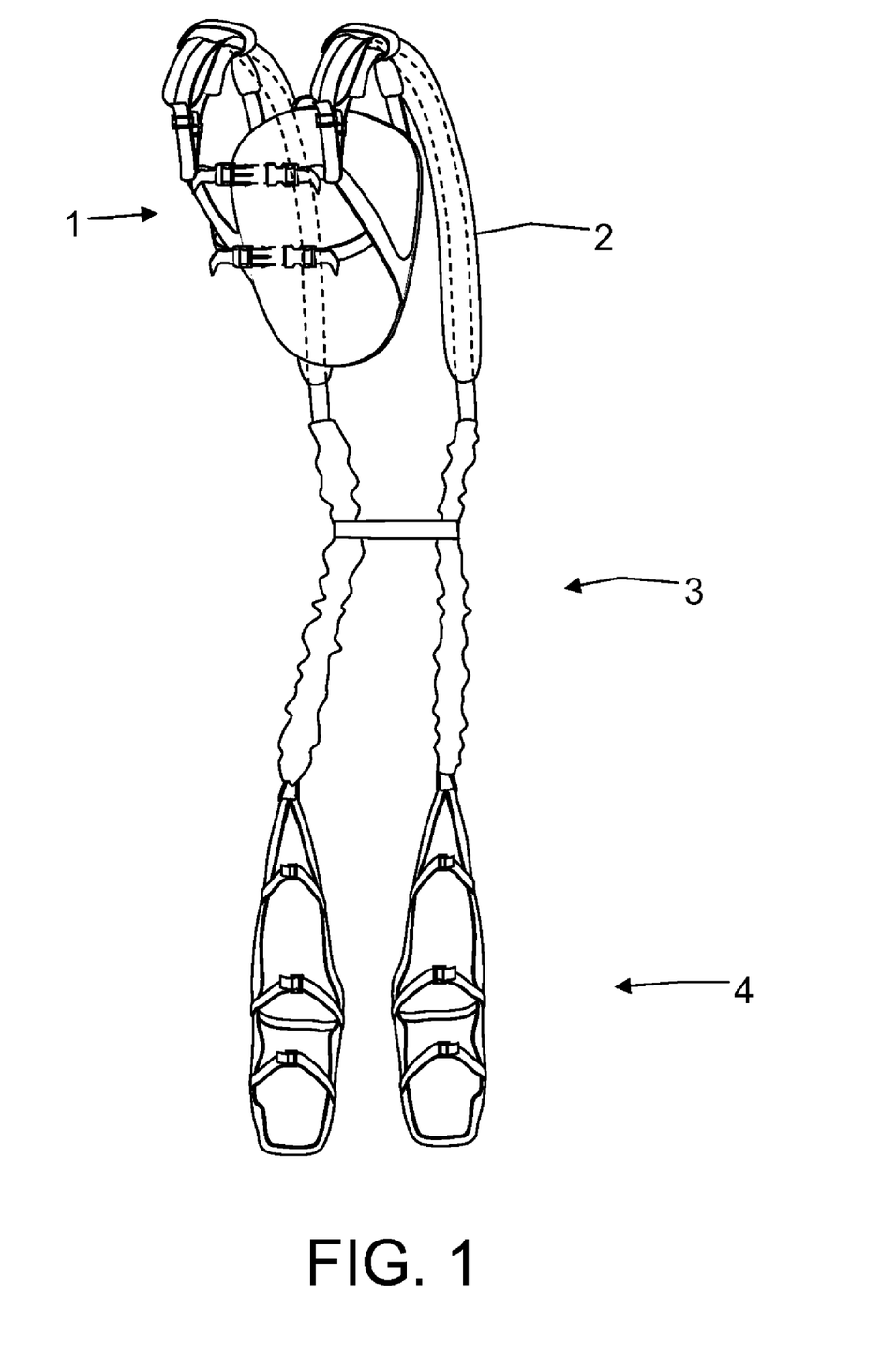
FIG. 1 illustrates the whole back support system.
Figure 2:
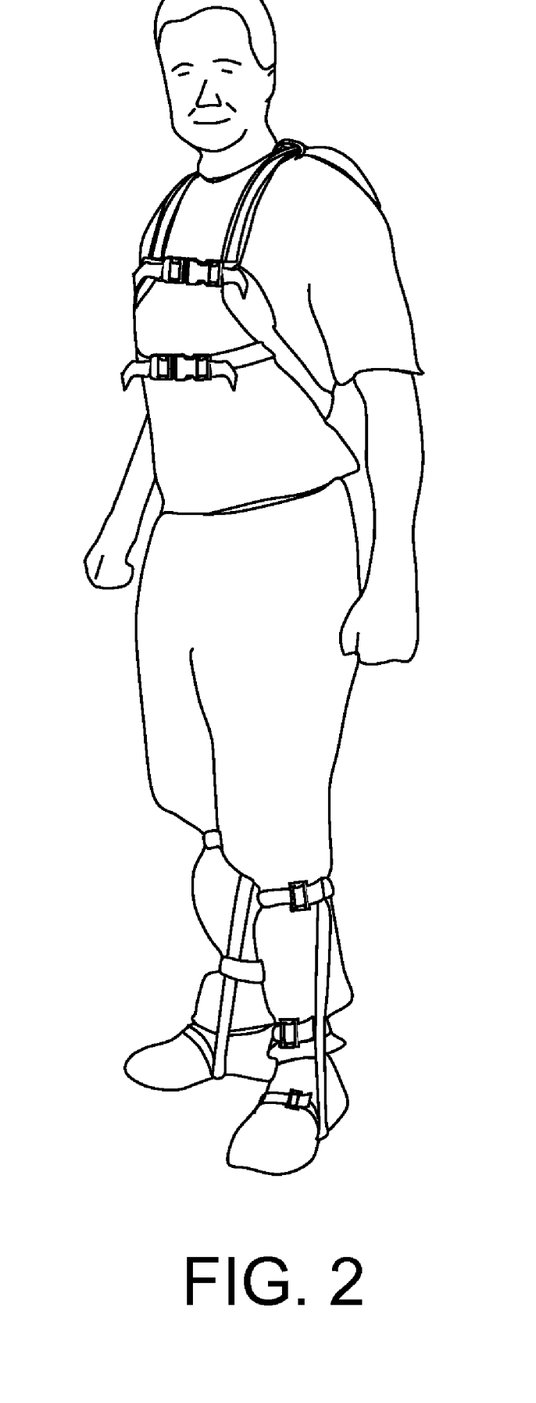
FIG. 2 provides a front view of a person wearing the back support system.
Figure 3:
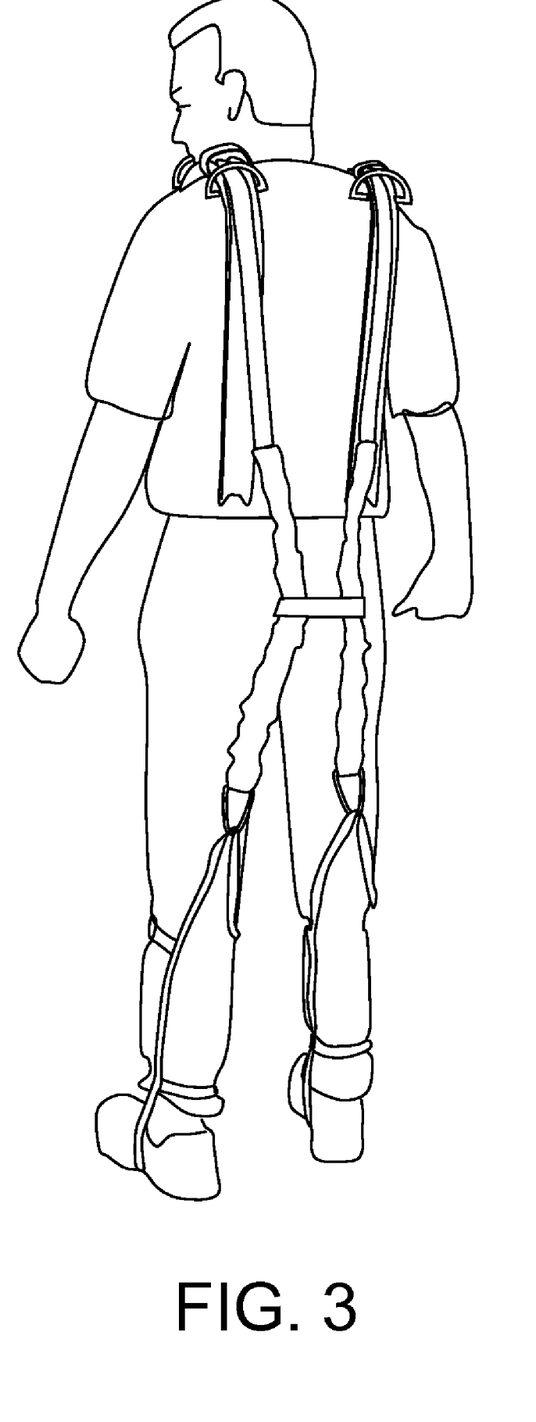
FIG. 3 provides a back view of a person wearing the back support system.

This invention is illustrated in FIG. 1. FIGS. 2 and 3 illustrate the device as it is worn by a person. It comprises the following parts
a) The harness 1
b) The yoke system 2
c) The tension system 3
d) The legging strap system 4

Harness

Figure 4:
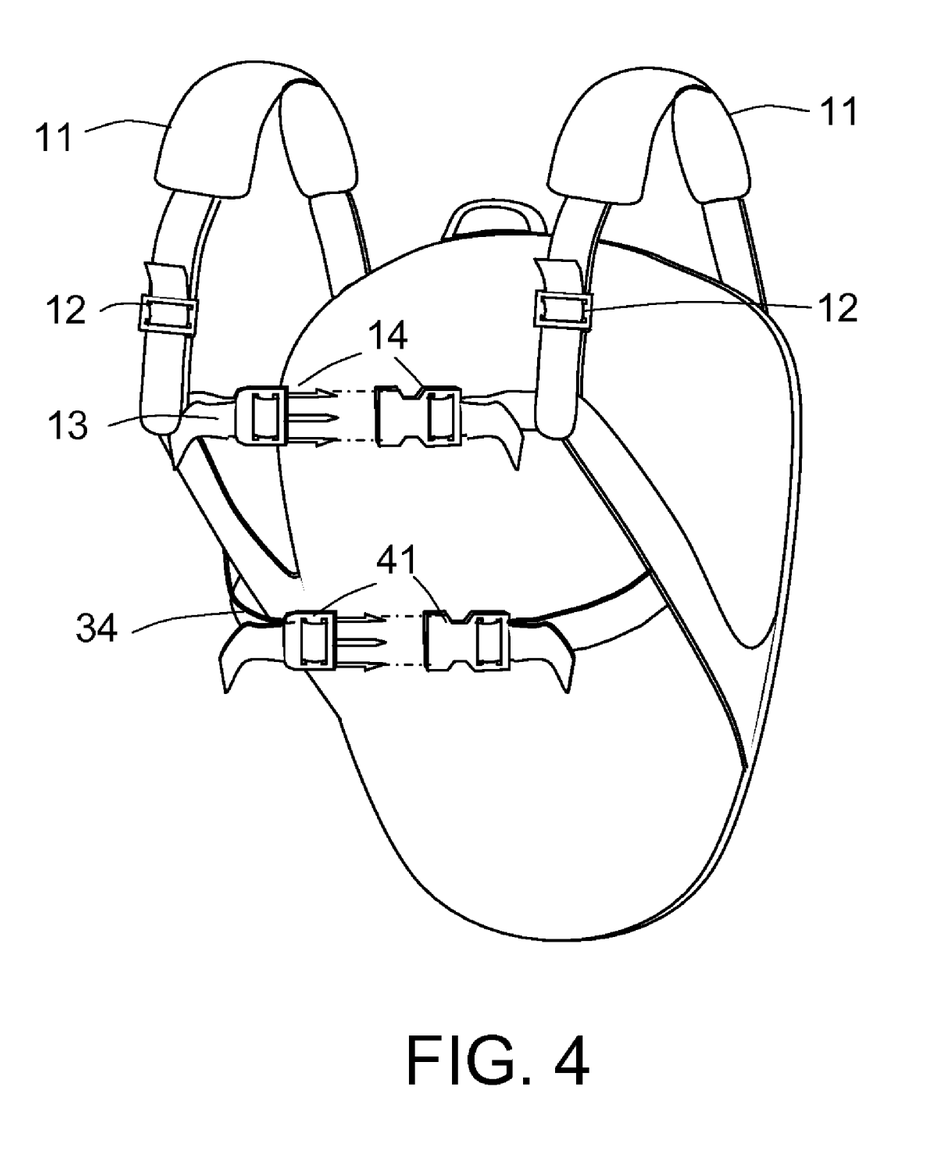
FIG. 4 illustrates the harness that wraps around the chest of the wearer.

This component is shown in FIG. 4. It resembles to a certain extent, a back-pack harness. It is made of a flexible, breathable mesh material attached to the chest of the wearer. Two padded shoulder straps 11 wrap over the shoulder of the wearer. These straps are equipped with adjusting buckles 12. Two additional straps 13 and 34 wrap around the chest of the wearer and are attached to the shoulder straps approximately at the breast location on the chest. These straps are equipped with adjusting and fastening buckles 14 and 41.

Yoke System

Figure 5:
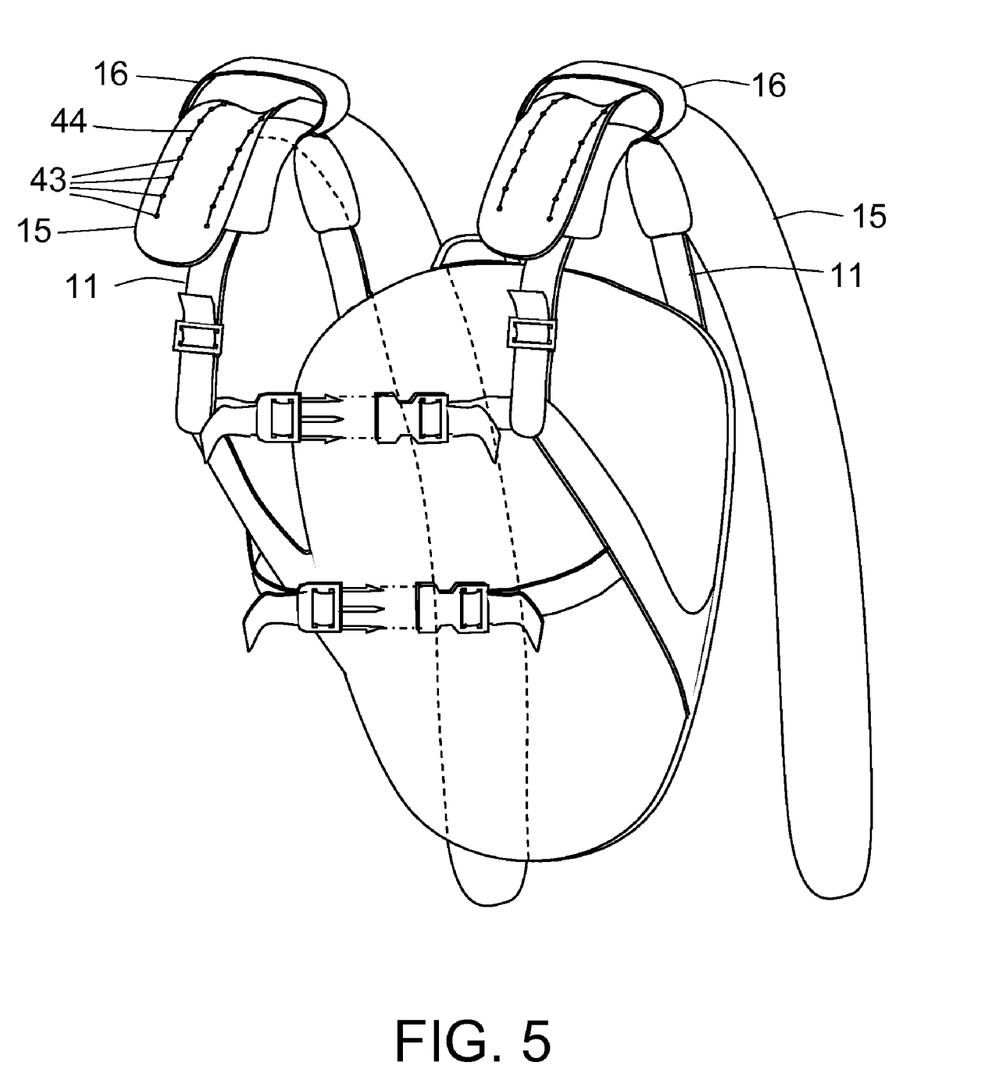
FIG. 5 shows how the yoke fits on top of the harness.

The yoke system 2 is shown in FIG. 5. It consists of two rigid curved rails 15 attached to the shoulder straps 11 and wrapping around the shoulders of the wearer. The two curved rails 15 fit on the top of the shoulder straps 11. They are designed to apply the load mainly to the skeleton of the wearer instead of onto his soft tissues. These rails are attached to the shoulder straps 11 by means of snap-on bands 16. Alternatively, the rails 15 can also be sewn to the shoulder straps 11. Sewing the rails 15 to the shoulder straps can be done, for example, by pre-drilling or pre-forming holes 43 in rows, each row oriented longitudinally along the rails 15, with each hole 43 separated approximately ¾" from each others. Thread 44 can then be passed through the holes 43 to sew the shoulder straps 11 securely to the rails 15. The rails 15 can be made of light plastic such as PVC. They can be detached as shown in FIG. 1.

Tension System

Figure 6:
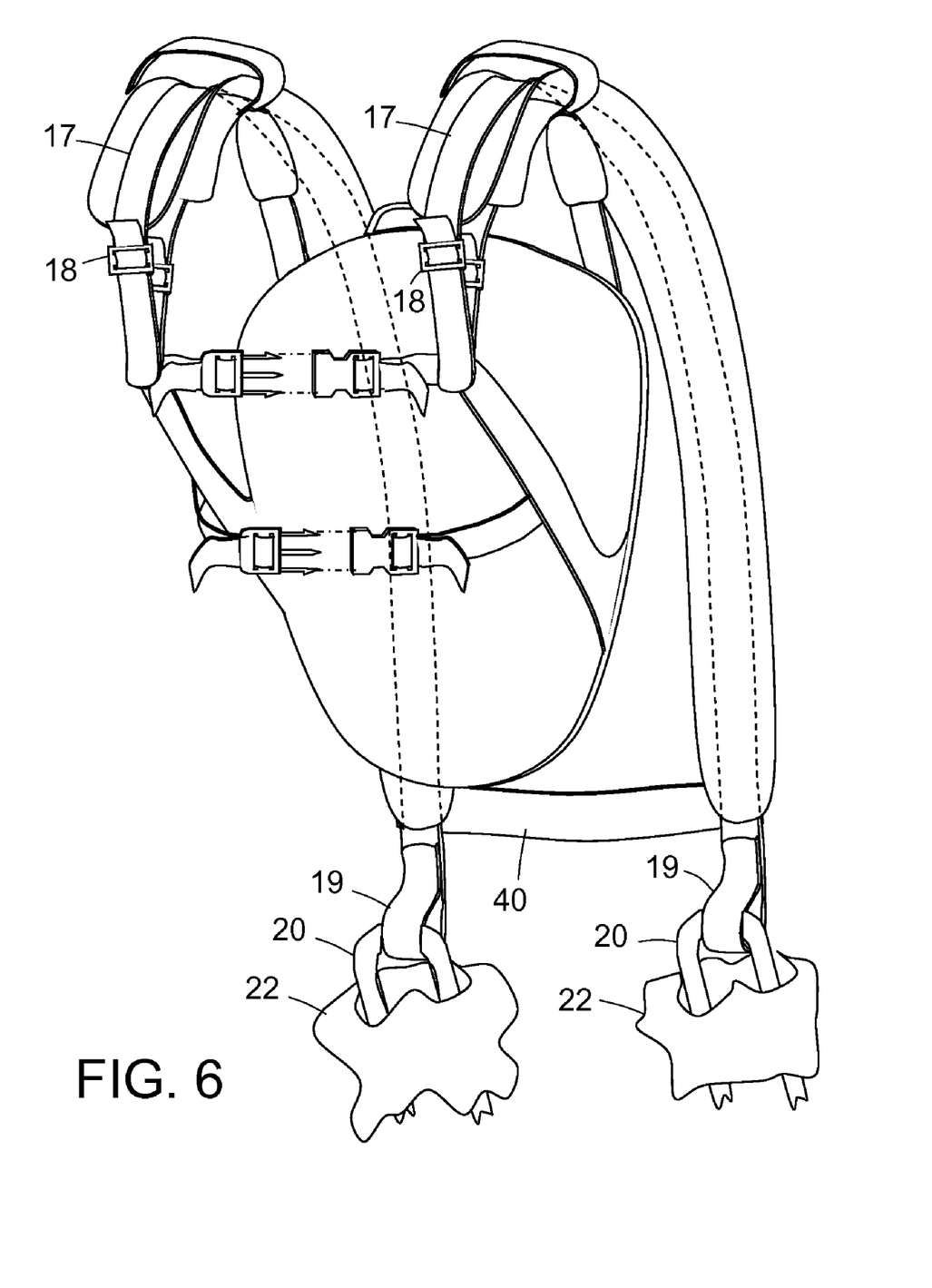
FIG. 6 illustrates how the tension straps fit over the yoke.
Figure 7:
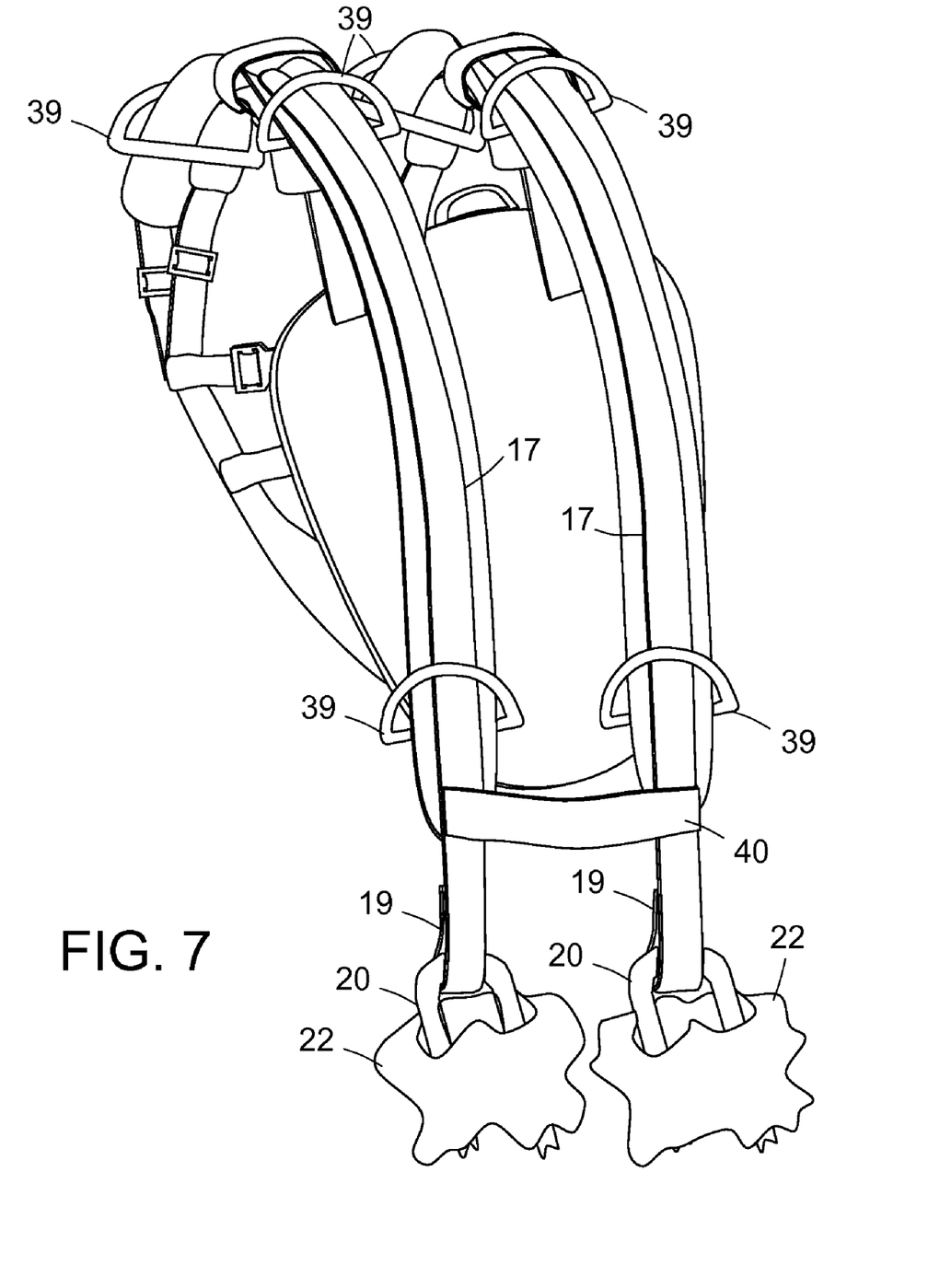
FIG. 7 provides a back view of the invention, showing how the tension straps attach to the elastic tubing.
Figure 8:
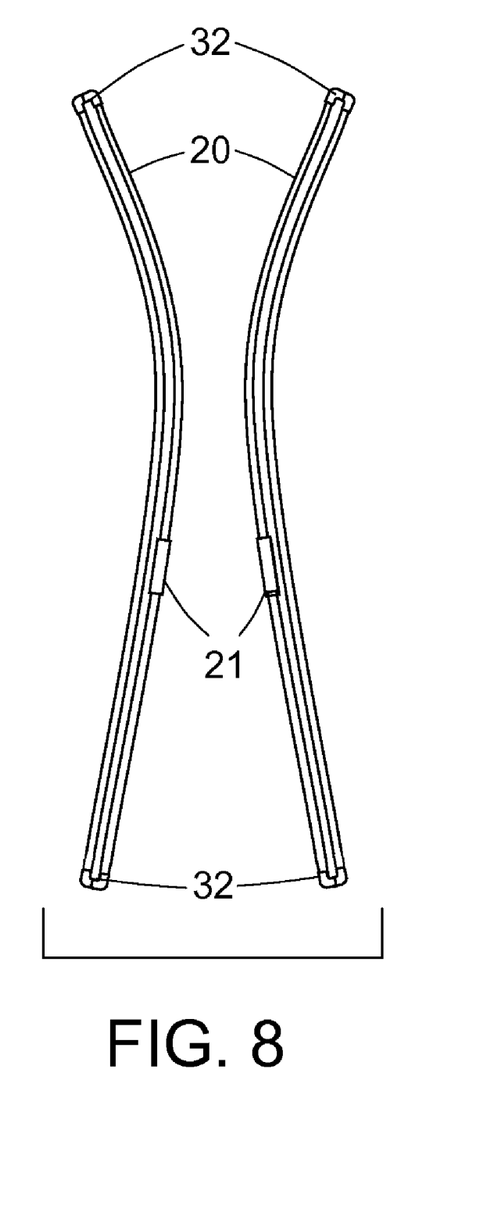
FIG. 8 shows the loops of surgical tubing.
Figure 8A:
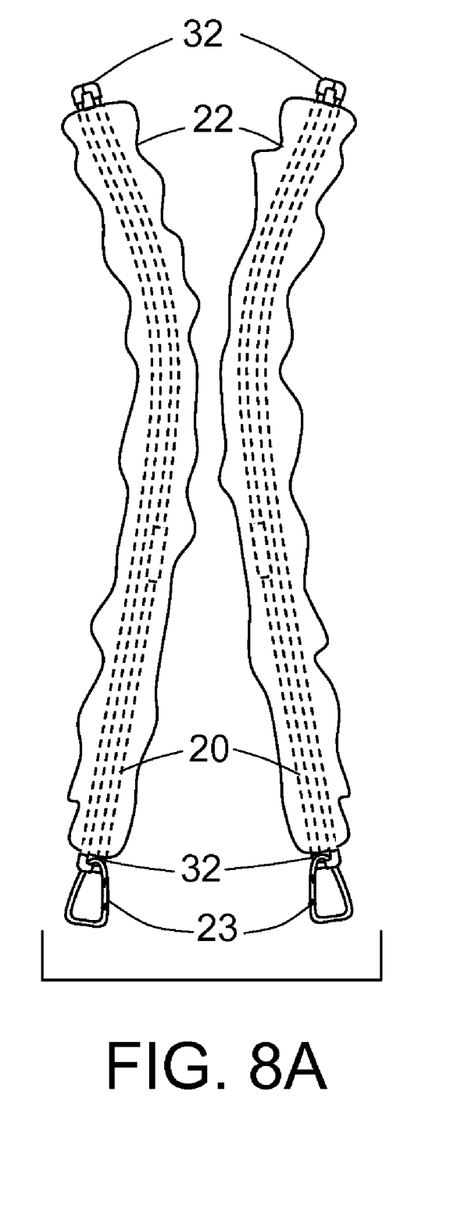
FIG. 8A shows how the surgical tubing is covered with fabric to protect it. It also shows the carabiners attached to one of the ends of the tubing.
Figure 9:
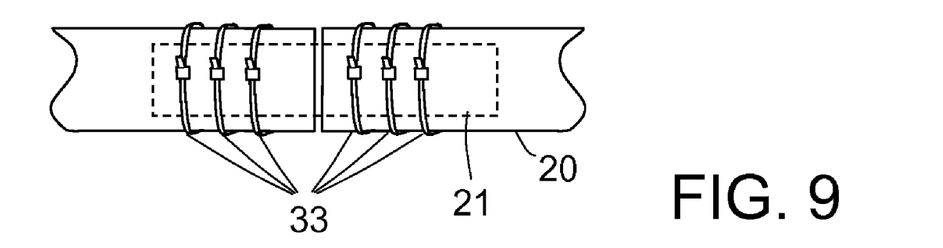
FIG. 9 illustrates how the ends of the surgical tubing are attached together by means of cable ties to form a loop.
Figure 9A:
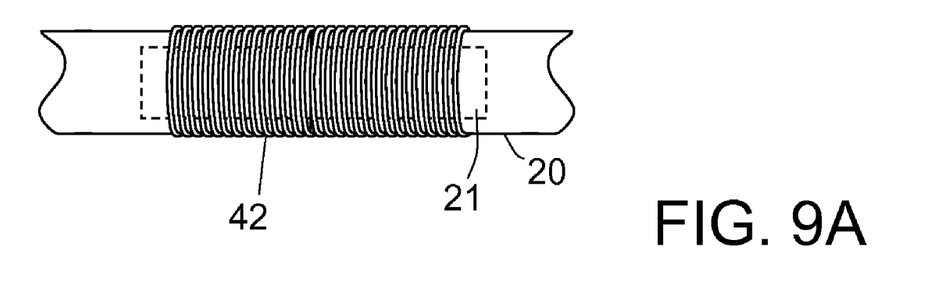
FIG. 9A illustrates how the ends of the surgical tubing are attached together by means of nylon cable to form a loop.

The tension system 3 is shown in FIGS. 6, 7 and 8. It is designed to provide an elastic tension that counterbalances the weight carried by the wearer of the device. It comprises the following components:
a) Two tension straps 17 shown in FIGS. 6 and 7, equipped with adjustable buckles 18. The straps are attached (for example sewn) at their top ends to the front of the harness 1. At their bottom ends, the straps form loops 19. D-shaped rings 39 may be used to hold the tension straps 17 in place inside the curved rails 15. In addition, the tension straps 17 can be joined together by means of a horizontal strap 40.
b) Elastic cables 20 shown in FIGS. 7 and 8 pass through the loops 19 formed by the straps 17. The cables 20 can be made from a diversity of elastic material. For example, it has been found convenient to use cables consisting of loops of surgical tubing made of latex. The tubing is formed into a loop by joining two ends of a tube segment. The joining of the ends can be done in many possible ways. For example as shown in FIG. 9, one can use for this purpose a cylinder 21 made of hard plastic and with a diameter slightly larger than the inner diameter of the tubing 20. The cylinder 21 would be threaded at both ends, with a clockwise screw at one end and a counterclockwise screw at the other end. The cylinder 21 would then be screwed inside the ends of the tubing 20 thus joining the two ends together. To provide additional binding, each tubing end could be clamped against the cylinder by means of at least one zip tie or cable tie 33. At their top ends, the loops of surgical tubing pass through the loops 19 located at the bottom of the straps 17. Alternatively, as illustrated in FIG. 9B, high tension nylon string 42 can be wound over and over the length of the coupling.

Figure 9B:
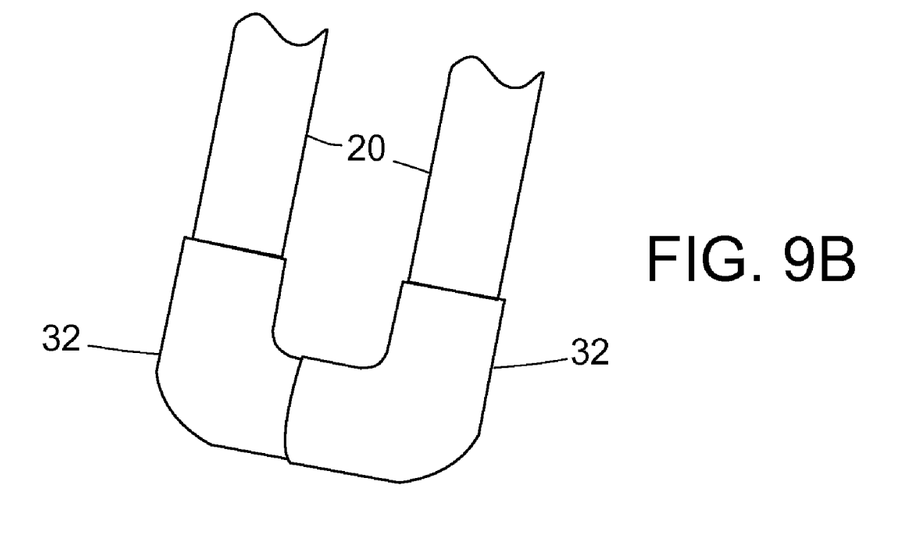
FIG. 9B shows how the surgical tubing is reinforced at the tips of the loop where it is attached to the tension straps and to the carabiners.

As illustrated in FIG. 9B, the elastic cables 29 are reinforced at the point of contact with the loops 19 by U-shaped rigid tubing 32 formed, for example, by assembling together two L-shaped copper tube elbows. The surgical tubing loop 20 is covered by a fabric sheath 22 to protect it and allow it to easily move during use. The bottom of the loops of surgical tubing 20 holds a carabiner 23 (as it is known in the trade) or a functionally equivalent device. It is a metal loop with a sprung or screwed gate which can quickly and reversibly connect components. The surgical tubing 20 is also reinforced at the point of contact with the carabiners 23 by U-shaped rigid tubing 32.

Optionally, as shown in FIG. 7 the tension straps 17 can be joined together by means of a horizontal strap 37.

Legging

Figure 10:
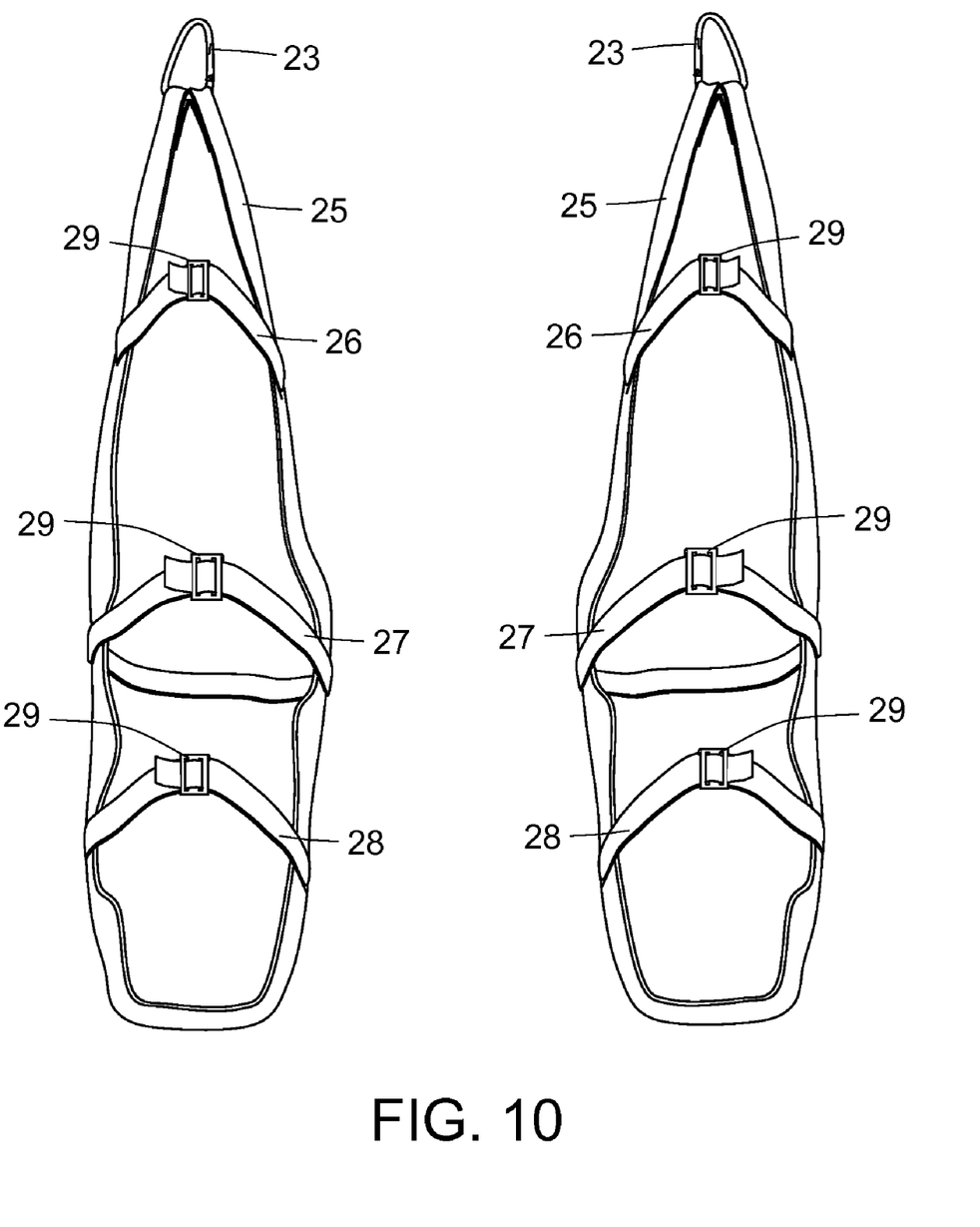
FIG. 10 illustrates the legging strap system.

Each carabiner 23 connects one of the surgical tubing loops 20 in the tension system 3 to a side of the legging strap system 4. A detailed view of the legging strap system 24 is shown in FIG. 10. It comprises a vertical strap 25 attached at both of its ends to a carabiner 23. This vertical strap 25 extends from the carabiner 23 and wraps around the wearer's shoe. The vertical strap 25 is held in place against the wearer's leg by means of several horizontal straps 26, 27 and 28. These straps comprise adjustable buckles 29 and are wrapped around the foot, the ankle and just below the knee of the wearer.

Transfer of Forces

An important aspect of this invention is how the forces are distributed. This feature can be illustrated by means of FIGS. 11 and 11A. One must note how the tension system 3 and the legging 4 follow the wearer's skeleton. As the wearer of the device bends over, the tension system 3 takes over tensile forces 35 allowing the skeleton of the wearer to experience mainly compressive forces 30. This configuration results in the least effort and stress on the wearer's part.

Figure 11:
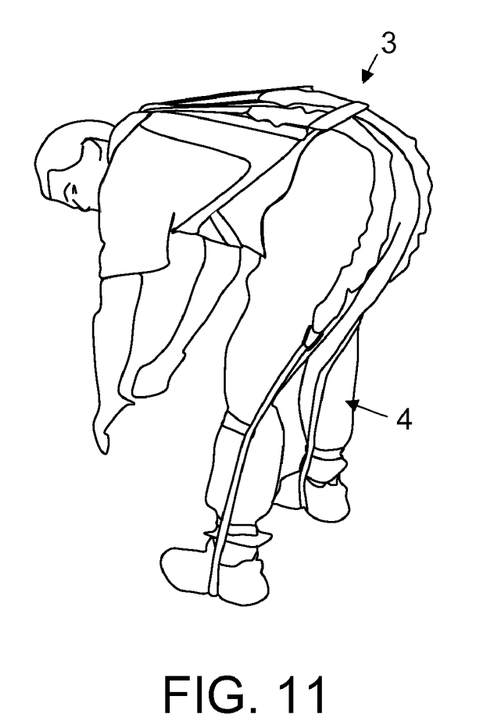
FIG. 11 shows the back support system is used when the wearer bends over.
Figure 11A:
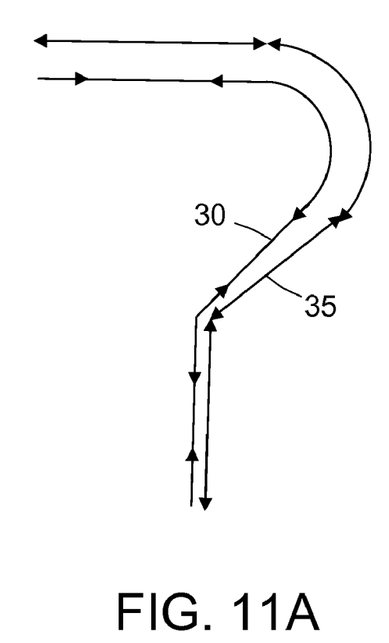
FIG. 11A provides a force diagram illustrating the force vectors acting on the wearer and on the back support system.

In addition, the yoke system 2 ensures that forces are applied to the wearer's skeleton rather than to his soft tissues.

Variations

As is evident to someone versed in the arts, many embodiments of this invention are possible. The straps 11, 13, 34, 17, 25, 26, 27 and 28 can be made of material such as nylon, Kevlar, leather or such similar material.

According to another variation, fastening buckles 14 and 41 can be replaced by VELCRO™ fasteners.

According to yet another variation, the surgical tubing loops 20 can be replaced by springs.

Figure 12:
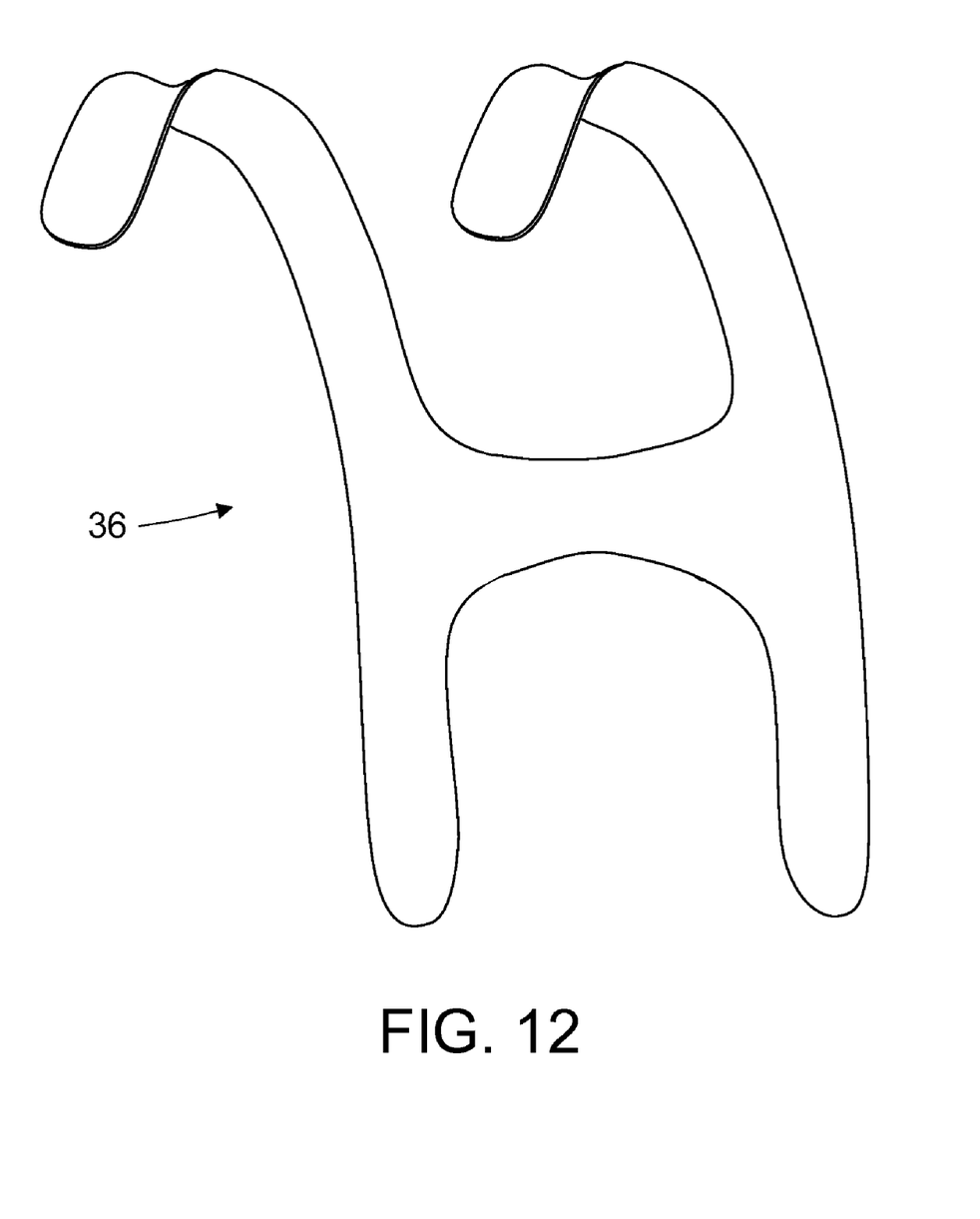
FIG. 12 shows how a yoke system can be shaped out of a single piece.

In a further variation illustrated in FIG. 12, the yoke system can be a single piece 37 instead of being two different pieces 15 as shown in FIG. 5.

Figure 13:
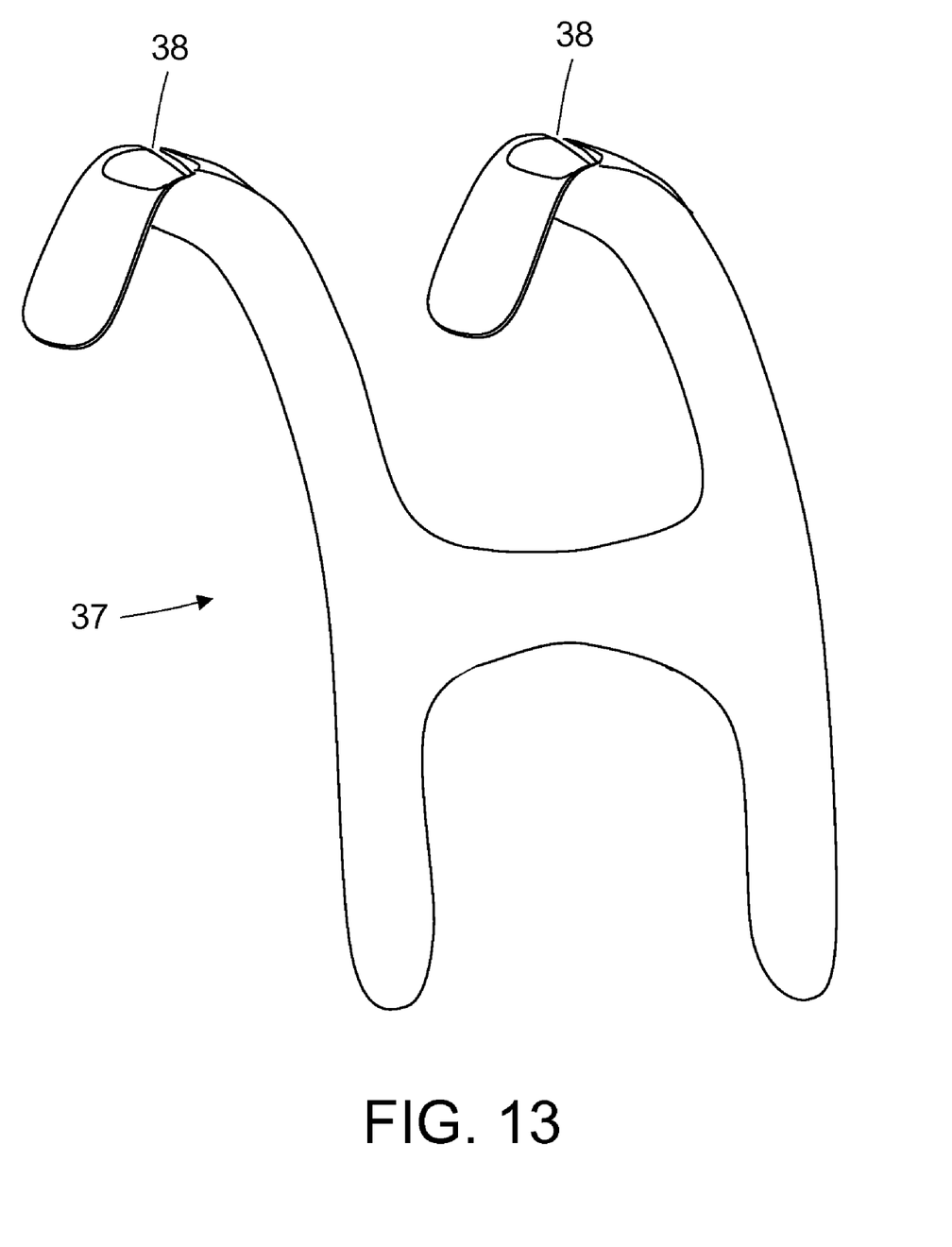
FIG. 13 illustrates how the functionality of the D rings can be implemented by shaping the rails in the yoke in the form of tubes slotted along their length.

In yet a further variation, the functionality of the D rings can be implemented by shaping the rails 15 in the yoke 37, in the form of tubes. The tubes may incorporate longitudinal slots 38 as shown in FIG. 13 or may be closed.

While the above description contains many specificities, the reader should not construe these as limitations on the scope of the invention, but merely as exemplifications of preferred embodiments thereof. Those skilled in the art will envision many other possible variations within its scope. Accordingly, the reader is requested to determine the scope of the invention by the appended claims and their legal equivalents, and not by the examples which have been given.

I claim:

1. A back support system for reducing stress exerted on a back of a wearer, said back support system comprising:
   a. a harness comprising breast straps, a right shoulder strap and a left shoulder strap, said harness being configured to be secured to the torso of said wearer by means of said breast straps joined at the front of said wearer's chest, and each said shoulder strap being configured to be wrapped from front to back, over the shoulders of said wearer;
   b. a yoke system comprising a right curved rail and a left curved rail, both said curved rails made of rigid material, said right curved rail attached to right said shoulder straps, said left curved rail attached to left shoulder strap, both said curved rails having their top surfaces configured in a concave shape in their perpendicular directions, both said curved rails being configured to wrap in their longitudinal directions over the shoulders of said wearer from front to back;
   c. a tension system comprising:
      i. a right tension strap and a left tension strap, said right tension strap configured to wrap from front to back inside the concave surface of said right curved rail and said left tension strap wrapping from front to back inside the concave surface of said left curved rail, both tension straps attached at their top ends to said breast straps at points located at said front of said wearer's chest;
      ii. a right elastic cable having a bottom and a left elastic cable having a bottom, said right elastic cable attached at its top end to said right tension strap and said left elastic cable attached at its top end to said left tension strap;
   d. a legging system comprising a left legging net and a right legging net, said left legging net comprising:
      i. a left vertical strap attached at its two ends to the bottom of said left elastic cable, said left vertical strap forming a left vertical loop, said left vertical loop being configured to wrap around the left sole of said wearer;
      ii. at least one horizontal left strap attached to said left vertical strap, said left vertical strap being configured to be fastened against the left leg of said wearer to force said left vertical strap to follow essentially the bone structure of said wearer's left leg;
      iii. at least one left foot strap attached to said left vertical strap, said left vertical strap being configured to be fastened against the left foot of said wearer; and
   said right legging net comprising:
      i. a right vertical strap attached at its two ends to the bottom of said right elastic cable, said right vertical strap forming a vertical loop, said right vertical loop being configured to wrap around the right sole of said wearer;
      ii. at least one horizontal right strap attached to said right vertical strap, said right vertical strap being configured to be fastened against the right leg of said wearer to force said right vertical strap to follow essentially the bone structure of said wearer's right leg;
      iii. at least one right foot strap attached to said right vertical strap, said right vertical strap being configured to be fastened against the right foot of said wearer;
   whereby said tension system generates a tension force when said wearer bends over to lift a load, said tension force counterbalancing the forces generated on back of said wearer by said load thereby relieving stress on his back, and whereby said tension system maintains said tensile force essentially aligned along the bone structure of his leg thereby relieving stress along his legs and furthermore wherein said yoke distributes forces generated by said load on the shoulder of said wearer.

2. The back support system as in claim 1 wherein said breast straps are equipped with adjusting and fastening buckles.

3. The back support system as in claim 1 wherein said shoulder straps are equipped with adjusting buckles.

4. The back support system as in claim 1 wherein said curved rails in said yoke system are configured in the shape of slotted tubes, said slotted tubes comprising a slot along their longitudinal direction.

5. The back support system as in claim 1 wherein each said elastic cables comprises a segment of surgical tubing, the ends of said segment being joined together to form a loop.

6. The back support system as in claim 5 wherein each said elastic cable is reinforced by a U-shaped rigid tube at the point of contact with said tension strap to which it is attached, and wherein each said segment of elastic cable is also reinforced by a U-shaped rigid tube at the point of contact with said legging net to which it is attached.

7. The back support system as in claim 6 wherein said U-shaped rigid tubes are formed by assembling together two L-shaped copper elbow tubes.

8. The back support system as in claim 5 wherein said surgical tubing have their ends joined together by a threaded cylinder made of rigid material, a first end of said cylinder being inserted into one end of said surgical tubing and a second end of said cylinder being inserted into a second end of said surgical tubing, and wherein said cylinder and surgical tubing are clamped together by means of at least two ties or cable ties.

9. The back support system as in claim 1 wherein each said segment of elastic cable is attached to said legging net by means of a carabiner.

10. The back support system as in claim 1 wherein said legging nets are equipped with at least one adjusting buckle.

11. The back support system as in claim 1 wherein said legging nets are equipped with at least one adjusting and fastening buckle.

12. The back support system as in claim 1 wherein at least one strap is equipped with an adjusting and fastening buckle.

13. The back support system as in claim 1 wherein at least one of said straps is equipped with hoop and loop fasteners.

14. The back support system as in claim 1 wherein said elastic cables are tension springs.

15. The back support system as in claim 1 wherein said rails are attached to said shoulder straps by means of D-shaped rings.

16. The back support system as in claim 1 wherein said tension straps are joined together at their lower ends by a horizontal strap.

17. The back support system as in claim 1 wherein said rails are sewn to said shoulder straps.

* * * * *